United States Patent
Trieu et al.

(10) Patent No.: US 11,571,530 B2
(45) Date of Patent: Feb. 7, 2023

(54) LIQUID STORE FOR AN INHALER, IN PARTICULAR FOR AN ELECTRONIC CIGARETTE PRODUCT

(71) Applicant: KÖRBER TECHNOLOGIES GMBH, Hamburg (DE)

(72) Inventors: Hoc Khiem Trieu, Westergellersen (DE); Karen Kalaydzhyan, Hamburg (DE)

(73) Assignee: KÖRBER TECHNOLOGIES GMBH, Hamburg (DE)

( * ) Notice: Subject to any disclaimer, the term of this patent is extended or adjusted under 35 U.S.C. 154(b) by 224 days.

(21) Appl. No.: 16/755,667

(22) PCT Filed: Oct. 11, 2018

(86) PCT No.: PCT/EP2018/077744
§ 371 (c)(1),
(2) Date: Apr. 13, 2020

(87) PCT Pub. No.: WO2019/072971
PCT Pub. Date: Apr. 18, 2019

(65) Prior Publication Data
US 2021/0186100 A1  Jun. 24, 2021

(30) Foreign Application Priority Data
Oct. 13, 2017 (DE) .................. 10 2017 123 869.7

(51) Int. Cl.
A24F 40/48 (2020.01)
A24F 40/42 (2020.01)
(Continued)

(52) U.S. Cl.
CPC ............. *A61M 15/06* (2013.01); *A24F 40/42* (2020.01); *A24F 40/48* (2020.01); *A24F 40/485* (2020.01); *A24F 40/51* (2020.01); *A24F 40/10* (2020.01)

(58) Field of Classification Search
CPC .......... A24F 40/10; A24F 40/42; A24F 40/48; A24F 40/51
See application file for complete search history.

(56) References Cited

U.S. PATENT DOCUMENTS

2010/0307518 A1  12/2010  Wang
2015/0027459 A1  1/2015  Collett et al.
(Continued)

FOREIGN PATENT DOCUMENTS

DE  20 2014 101 125 U1  6/2014
DE  10 2014 114 133 A1  3/2016
(Continued)

OTHER PUBLICATIONS

1st Examination Report issued by the German Patent and Trademark Office dated Oct. 13, 2017 with respect to priority German Patent Application No. 10 2017 123 869.7.
(Continued)

*Primary Examiner* — Hae Moon Hyeon
(74) *Attorney, Agent, or Firm* — Saliwanchik, Lloyd & Eisenschenk (57) ABSTRACT

The invention relates to a liquid store for an inhaler (10), in particular for an electronic cigarette product, having an outlet end (53) which can be fluidically connected to a heating element (60) in order to evaporate liquid (50) supplied to the heating element (60) from the liquid store (18). The liquid store (18) has at least one air inlet end (52) and at least one channel (51). The channel (51) extends from the air inlet end (52) to the outlet end (53) through the liquid (Continued)

store (18), wherein the channel (51) is designed to transfer the liquid (50) stored in the liquid store (18) to the outlet end (53) through the channel (51) via capillary forces.

20 Claims, 3 Drawing Sheets

(51) Int. Cl.
    *A61M 15/06*     (2006.01)
    *A24F 40/485*    (2020.01)
    *A24F 40/51*     (2020.01)
    *A24F 40/10*     (2020.01)

(56) References Cited

U.S. PATENT DOCUMENTS

| | | |
|---|---|---|
| 2015/0245654 A1 | 9/2015 | Memari et al. |
| 2017/0071254 A1 | 3/2017 | Revell |
| 2017/0231284 A1 | 8/2017 | Newns |
| 2018/0146711 A1* | 5/2018 | Mazur ............... F04B 43/043 |
| 2020/0128874 A1* | 4/2020 | Atkins ............... A24F 40/42 |
| 2020/0329769 A1 | 10/2020 | Liu |
| 2022/0007722 A1* | 1/2022 | Valentine ............ A24F 40/42 |

FOREIGN PATENT DOCUMENTS

| | | |
|---|---|---|
| EP | 0 845 220 A1 | 6/1998 |
| EP | 3127441 A1 | 2/2017 |
| JP | 2000-041654 A | 2/2000 |
| JP | 2007-232669 A | 9/2007 |
| JP | 2010-526553 A | 8/2010 |
| JP | 2016-525367 A | 8/2016 |
| JP | 2017-523785 A | 8/2017 |
| WO | WO 2016/064684 A1 | 4/2016 |
| WO | WO 2016/096780 A1 | 6/2016 |
| WO | WO 2018/083007 A1 | 5/2018 |

OTHER PUBLICATIONS

Communication received from the U.S. Patent Office dated Jul. 15, 2021 regarding a Third Party Submission submitted to the U.S. Patent Office on Jul. 13, 2021.

Third-Party Submission under 37 CFR 1.290 and concise description of relevance.

Office Action issued by the Japanese Patent Office dated Nov. 25, 2022 for parallel Japanese patent application No. 2020-520585.

\* cited by examiner

Fig. 7

LIQUID STORE FOR AN INHALER, IN PARTICULAR FOR AN ELECTRONIC CIGARETTE PRODUCT

CROSS REFERENCE TO RELATED APPLICATIONS

This application is a National Stage Application of International Application Number PCT/EP2018/077744, filed Oct. 11, 2018; which claims priority to German Patent Application No. 10 2017 123 869.7, filed Oct. 13, 2017.

FIELD OF THE INVENTION

The present invention relates to a liquid store for an inhaler, in particular for an electronic cigarette product, having an outlet end which can be fluidically connected to a heating element in order to evaporate liquid supplied to the heating element from the liquid store.

BACKGROUND OF THE INVENTION

A large number of electronic cigarette products are known in the prior art, in which the liquid store is either designed as a reservoir or a tank, or in which the liquid is stored in a sponge, for example made of acetate. In both cases, the reservoir communicates with the outside world at least via a wick and the heating element, which is arranged in an air channel that is open to the outside and is in pressure equilibrium with the outside world.

Both variants described above have the disadvantage of leakage. On the one hand, liquid can escape if there is a marked change in the ambient pressure, for example in an aircraft. On the other hand, if the evaporator function is not available, for example when the energy store of the electronic cigarette product is empty, the user can suck the liquid directly out of the liquid store by means of a puff and the resulting negative pressure. This is unpleasant and leads to irritation in the mouth region.

In the prior art, there is still partial or complete dry running of the evaporator unit and insufficient wetting of the surface of the evaporator. In both cases, the lack of cooling caused by the liquid to be evaporated results in temperatures above 250° C., which leads to the formation of harmful substances through decomposition and radicalisation of the liquid components, especially glycerol and propylene glycol. Due to an uncontrolled or undetected supply and evaporation of liquid, the quality of the aerosol produced is unintentionally and uncontrollably influenced.

BRIEF SUMMARY

The object of the invention is to provide a liquid store which allows leak-free and safe storage, reliable replenishment of liquid and a level measurement independent of gravity, regardless of the orientation of the liquid store during use.

The invention achieves said object by means of the features of the independent claims.

According to the basic idea of the invention, it is proposed that the liquid store has at least one air inlet end and at least one channel, and the channel extends from the air inlet end through the liquid store to the outlet end, wherein the channel is designed to convey the liquid stored in the liquid store to the outlet end through the channel by means of capillary forces. Accordingly, an in particular microfluidic liquid store is proposed, from which, over the entire volume of the reservoir, liquid can be fed to a heating element in a controllable manner, either actively or passively, at a regular rate, regardless of gravity and in particular regardless of orientation. The channel extends through the liquid store and serves both to store and to convey the liquid. The liquid transport through the reservoir or the channel takes place on the basis of capillary forces and/or with the targeted use of Laplace pressure.

Capillary forces arise when liquid is removed from the outlet end in order to supply it to the heating element, and the remaining liquid follows the pressure drop and air flows in at the air inlet end in order to equalise the pressure.

In this way, the invention permits a fill level monitoring of the liquid store that is independent of gravity. The force of gravity is typically considerably smaller than the capillary forces acting on the liquid in the liquid store according to the invention. Thus, the liquid in the liquid store is kept independent of gravity and, in particular, independent of orientation, which allows reliable fill level monitoring.

Furthermore, the forces that a consumer can apply to the inhaler by means of a puff are typically considerably smaller than the capillary forces that serve to convey the liquid, and thus the consumer can be prevented from drawing liquid out of the evaporator unit without said liquid being evaporated.

The liquid store preferably has an in particular capacitive and/or resistive fill level sensor which has at least one measuring electrode arranged along the at least one channel. A capacitive level sensor along the at least one channel allows the exact and reliable determination of the fill level of the liquid in the liquid store and/or in the at least one channel. The liquid in the liquid store serves as a dielectric for the capacitive measurement of the fill level. The capacitance is determined by the dielectric and is therefore clearly dependent on the fill level of the liquid in the liquid store.

In a preferred embodiment, the measuring electrode is formed by an electrically conductive part of the liquid store. A particularly inexpensive and space-saving embodiment integrates the electrode into the liquid store. The at least one channel is delimited by channel walls and these can have and/or form the electrode. The at least one measuring electrode can be strip-shaped, for example, or be given by at least one measuring point. The channel walls are preferably electrically conductive, for example in that they consist of an electrically conductive material or have an electrically conductive coating, and form the measuring electrode. The channel walls may allow a capacitive measurement of the liquid level in portions, but at least on the outlet side, at one or more measuring points and/or measuring strips.

A semipermeable seal and/or filter layer is preferably arranged on the at least one air inlet end, wherein the semipermeable seal and/or the filter layer is air-permeable and liquid-impermeable. The semipermeable seal and/or filter layer counteracts the leakage of the liquid store by inhibiting or preventing the passage of liquid through the air inlet end. The air permeability of the semipermeable seal and/or filter layer allows pressure equalisation in the channel, which is necessary when withdrawing liquid at the outlet end, in order to ensure continuous liquid delivery and to prevent the development of a negative pressure.

It is advantageous that the liquid store has a plurality of channels in order to provide a sufficiently large volume for the storage of liquid and to promote the capillary transport of liquid. The volume of the liquid store is given by the volume of the channel or the volumes of the channels. The capillary forces can result from the cross section of the channel or the cross sections of the channels. The use of a plurality of channels in the liquid store can therefore serve to provide a liquid store with a sufficiently large total volume and at the same time a reliable supply of liquid. The plurality of channels can be arranged in the form of pores or holes as an array and/or can be cylindrically coaxial, interlocking or interlocking in portions.

The at least one channel is preferably formed between at least two housing parts of the liquid store, each of which has at least one channel wall, the channel walls interlocking in a comb-like manner when the housing parts are assembled in order to ensure the most cost-effective, simple and effective assembly possible and to achieve a definable volume of the liquid store with capillary forces which can be specifically adjusted during assembly. The comb-like interlocking channel walls engage in one another in such a way that a volume for the liquid, that is to say the at least one channel, is formed between the channel walls.

The geometry of the housing parts and their spacing in the assembled state determine the volume and the cross section of the at least one channel and thus the capillary forces acting therein. In this embodiment, one housing part can have and/or form in each case a measuring electrode in order to allow a simple, reliable and comprehensive capacitive and/or resistive measurement of the fill level of the liquid store.

In a preferred embodiment, the housing parts consist of an electrically conductive material or are coated with an electrically conductive material in order to allow for electrodes to be integrated as effectively and simply as possible in order to monitor the liquid level. The housing parts can, for example, be produced from a plastics material and then be at least partially coated and/or vapour-coated in order to be electrically conductive.

In a preferred embodiment, the at least one channel has regions of different hydrophilicity and/or hydrophobicity in order to specifically influence the transport of liquid through the channel. In other words, channel walls which form the at least one channel have regions of different hydrophilicity and/or hydrophobicity. The liquid has aqueous constituents and can be specifically controlled by the regions of different hydrophilicity and/or hydrophobicity.

The at least one channel preferably has a lower hydrophilicity at the air inlet end than at the outlet end in order to inhibit the escape of liquid at the air inlet end and to promote the escape of liquid at the outlet end. In other words, the walls of the reservoir, or of the at least one channel, are more hydrophobic than the heater-side outlet opening in order to promote the transport of the water-containing liquid in the direction of the outlet opening.

The at least one channel at the air inlet end is preferably hydrophobic in order to inhibit and/or prevent the unwanted escape of water-containing liquid at the air inlet end. The hydrophobic air inlet end promotes the sealing effect and prevents leakage of the liquid store.

It is advantageous that the at least one channel at the outlet end is hydrophilic in order to promote the escape at and/or the transport to the outlet end of water-containing liquid. At the outlet end, the liquid can be withdrawn by a capillary force and thus passively and/or by means of pumps and/or valves and thus actively.

One aspect of the invention relates to a consumption unit comprising the liquid store and an evaporator unit having the electrically operable heating element, wherein the heating element is designed to evaporate liquid supplied from the liquid store to the heating element by applying a heating voltage.

A wick structure is preferably arranged between the heating element and the liquid store, the wick structure being set up to receive fluid from the at least one outlet end of the fluid store and to convey it to the heating element by means of capillary forces. The wick serves for the passive removal of liquid at the at least one outlet end and for the build-up of a negative Laplace pressure, which requires the subsequent delivery of liquid.

The wick structure preferably covers the outlet end or all of the outlet ends in order to prevent leakage and to promote a uniform transport of liquid to the heating element from the liquid store via the wick.

At least one capacitive and/or resistive sensor for detecting liquid is preferably arranged on the heating element in order to characterise the operating state of the heating element and/or to determine the presence and/or amount of liquid to be evaporated. By means of a metallic sensor, for example, in the immediate vicinity of the heating element, preferably directly below a flat heating element, more preferably with direct contact to the liquid which is fed to the heating element and preferably within the capillary wick material which supplies the liquid to the heating element, liquid detection can take place on the heating element.

At least one in particular resistive temperature sensor for measuring the temperature of the heating element and/or the air flowing past the heating element is preferably set up on the heating element in order to characterise the operating state in the direct vicinity of the heating element and/or to detect overheating and/or undercooling of the heating element or of the liquid to be evaporated. The additional temperature element is used to check the cooling function of the ambient air flowing past the heating element and thus directly to measure the air temperature. The air temperature has an influence on the recondensation behaviour of the aerosol. Knowledge of the air temperature thus allows a prediction of the probable droplet sizes, taking into account the parameters set on the evaporator, or the adaptation of these parameters to influence the droplet size.

In order to allow for a compact design of the temperature sensor, said sensor preferably has a meandering shape. It is also possible for the temperature sensor to be formed by the heating element.

At least one of the sensors is preferably arranged as a conductor track on a carrier and more preferably on the same side of the carrier as the heating element, in order to allow an efficient construction and a targeted measurement.

BRIEF DESCRIPTION OF THE FIGURES

The invention will be explained below on the basis of the preferred embodiments with reference to the accompanying drawings. In the drawings.

DETAILED DESCRIPTION

Figure 1:
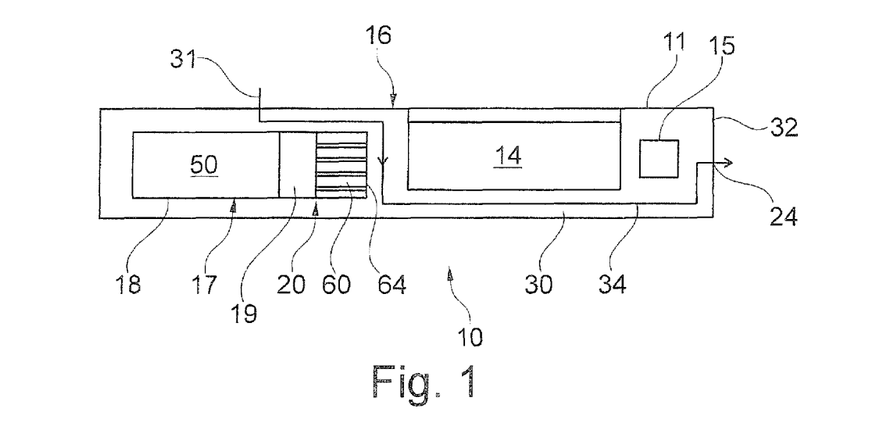
FIG. 1 is a schematic representation of an electronic cigarette product.

The inhaler 10, in this case an electronic cigarette product, comprises a housing 11 in which an air channel 30 is provided between at least one air inlet opening 31 and one air outlet opening 24 at a mouth end 32 of the inhaler 10. The mouth end 32 of the inhaler 10 is the end at which the consumer puffs for the purpose of inhalation and thereby applies a negative pressure to the inhaler 10 and generates an air flow 34 in the air channel 30.

The inhaler 10 consists advantageously of a base part 16 and a consumable unit or cartridge 17, which comprises the evaporator unit 20 and the liquid store 18 and is designed in particular in the form of an exchangeable cartridge. The air sucked in through the inlet opening 31 is conducted in the air channel 30 to or along at least one evaporator unit 20. The evaporator unit 20 is connected or can be connected to at least one liquid store 18 in which at least one liquid 50 is stored. The evaporator unit 20 evaporates liquid 50, which is supplied thereto from the liquid store 18, and adds the evaporated liquid as aerosol/vapour to the air flow 34 at an outlet side 64. An advantageous volume of the liquid store 18 lies in the range between 0.1 ml and 5 ml, preferably between 0.5 ml and 3 ml, more preferably between 0.7 ml and 2 ml or 1.5 ml.

The inhaler 10 also comprises an electrical energy store 14 and an electronic control device 15. The energy store 14 is usually arranged in the base part 16 and can be, in particular, a disposable electrochemical battery or a rechargeable electrochemical battery, for example a lithium-ion battery. The electronic control device 15 comprises at least one digital data processing apparatus, in particular a microprocessor and/or microcontroller, in the base part 16 (as shown in FIG. 1) and/or in the consumable unit 17.

A sensor, such as a pressure sensor or a pressure or flow switch, is advantageously arranged in the housing 11, wherein the electronic control device 15 can determine, on the basis of a sensor signal output from the sensor, that a consumer is puffing the inhaler 10 at the mouth end 32 in order to inhale. In this case, the electronic control device 15 triggers the evaporator unit 20 to add liquid 50 from the liquid store 18 as aerosol/vapour into the air stream 34.

The liquid 50 stored in the liquid store 18 to be dosed is, for example, a mixture of 1,2-propylene glycol, glycerol, water, at least one flavour and/or at least one active substance, in particular nicotine.

The consumable unit 17 advantageously comprises a non-volatile data store for storing information or parameters relating to the consumable unit or cartridge 17. The data store may be part of the electronic control device 15. The data store is advantageously used to store information regarding the composition of the liquid 50 stored in the liquid store 18, information regarding the process profile, in particular power/temperature control; data for condition monitoring or system testing, for example seal testing; data regarding copy protection and counterfeit protection, an ID for unique identification of the consumable unit or cartridge 17, serial number, date of manufacture and/or expiry date, and/or number of puffs (number of inhalation puffs by the consumer) or the period of use. The data store is advantageously connected or can be connected to the control unit 15 by means of contacts and/or conduits.

Figure 2:
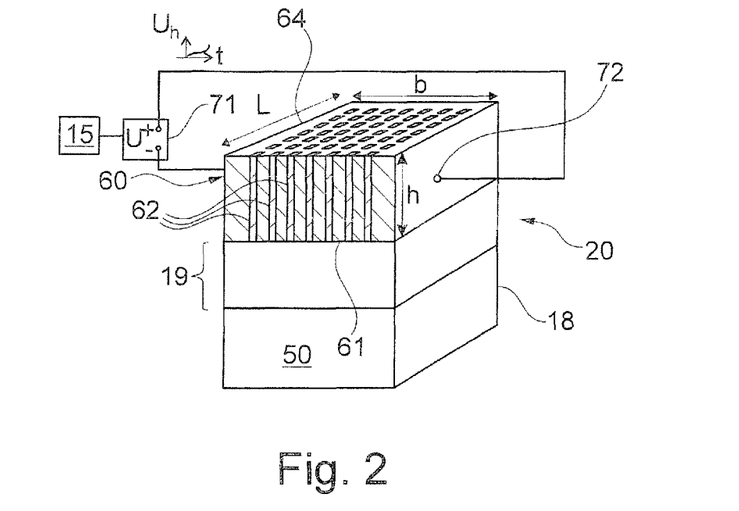
FIG. 2 is a schematic perspective cross-sectional view of an evaporator unit with a liquid store according to the invention.

An advantageous embodiment of an evaporator unit 20 according to the invention is shown in FIG. 2. The evaporator unit 20 comprises a block-shaped, preferably monolithic heating element 60 made of an electrically conductive material, preferably silicon, doped ceramic, metal ceramic, filter ceramic, semiconductor, in particular germanium, graphite, semimetal and/or metal. It is not necessary for the entire heating element 60 to be made of an electrically conductive material. It may be sufficient, for example, that the surface of the heating element 60 is coated in an electrically conductive manner, for example has a metallic coating. In this case, the entire surface does not have to be coated, for example conductor tracks can be provided on a non-conductive base element.

The heating element 60 is provided with a plurality of microchannels 62, which fluidically connect an inlet side 61 of the heating element 60 to an outlet side 64. The inlet side 61 is fluidically connected to the liquid store 18 via a wick structure 19. The wick structure 19 is used for the passive conveyance of liquid from a liquid store 18 to the heating element 60 by means of capillary forces. The wick structure 19 in the contact region of the inlet side 61 of the heating element 60 serves to distribute liquid evenly, to be temperature-resistant and to form a kind of check valve with its relatively small pores and/or thin capillaries in order to prevent undesirable backflow of bubbly liquid from the heating element 60 into the wick structure 19 and/or into the liquid store 18.

The median diameter of the microchannels 62 is preferably in the range between 5 μm and 200 μm, more preferably in the range between 30 μm and 150 μm, even more preferably in the range between 50 μm and 100 μm. Due to these dimensions, a capillary effect is advantageously produced, so that liquid penetrating into a microchannel 62 at the inlet side 61 rises upwards through the microchannel 62 until the microchannel 62 is filled with liquid. The volume ratio of the microchannels 62 to the heating element 60, which can be referred to as the porosity of the heating element 60, is for example in the range between 10% and 50%, advantageously in the range between 15% and 40%, more advantageously in the range between 20% and 30%, and is 25%, for example.

The edge lengths of the surfaces of the heating element 60 provided with microchannels 62 are, for example, in the range between 0.5 mm and 3 mm. For example, the dimensions of the surfaces of the heating element 60 provided with microchannels 62 can be as follows: 0.95 mm×1.75 mm or 1.9 mm×1.75 mm or 1.9 mm×0.75 mm. The edge lengths of the heating element 60 can be, for example, in the range between 0.5 mm and 5 mm, preferably in the range between 0.75 mm and 4 mm, more preferably in the range between 1 mm and 3 mm. The surface of the heating element 60 (chip size) can be, for example, 1 mm×3 mm or 2 mm×3 mm.

The width b of the heating element 60 (see FIG. 2) is preferably in the range between 1 mm and 5 mm, more preferably in the range between 2 mm and 4 mm, and is, for example, 3 mm. The height h of the heating element 60 (see FIG. 2) is preferably in the range between 0.05 mm and 1 mm, more preferably in the range between 0.1 mm and 0.75 mm, even more preferably in the range between 0.2 mm and 0.5 mm, and is, for example, 0.3 mm.

The number of microchannels 62 is preferably in the range between four and 1000. This allows the heat input into the microchannels 62 to be optimised and ensures a high evaporation capacity and a sufficiently large vapour outlet surface.

The microchannels 62 are arranged in the form of a square, rectangular, polygonal, round, oval or differently shaped array. The array may be in the form of a matrix having s columns along the width b of the heating element 60 and z rows along a length L of the heating element 60, wherein s is advantageously in the range between 2 and 50 and further advantageously in the range between 3 and 30 and/or z is advantageously in the range between 2 and 50 and further advantageously in the range between 3 and 30.

This allows for an effective and easily manufactured arrangement of microchannels 62 having a guaranteed high evaporation capacity.

The cross section of the microchannels 62 can be square, rectangular, polygonal, round, oval or otherwise shaped and/or can vary lengthwise in portions, in particular may increase, decrease or remain constant.

The length of one or each microchannels 62 is preferably in the range between 100 μm and 1000 μm, more preferably in the range between 150 μm and 750 μm, even more preferably in the range between 180 μm and 500 μm, and is, for example, 300 μm. This allows an optimum liquid absorption and a portion formation with sufficient heat input from the heating element 60 into the microchannels 62.

The distance between two microchannels 62 is preferably at least 1.3 times the clear diameter of one microchannel 62, wherein the distance refers to the centre axes of the two microchannels 62. The distance can preferably be 1.5 to 5 times the clear diameter of a microchannel 62, more preferably 2 to 4 times. In this way, an optimal heat input into the microchannels and a sufficiently stable arrangement and wall thickness of the microchannels can be realised.

The evaporator unit 20 has a heating voltage source 71, preferably controllable by the electronic control device 15, which is connected via electrodes 72 to opposite sides of the heating element 60, in such a manner that an electrical voltage Uh produced by the heating voltage source 71 leads to a current flow through the heating element 60. Due to the ohmic resistance of the electrically conductive heating element 60, the current flow leads to heating of the heating element 60 and therefore to evaporation of the liquid 50 contained in the microchannels 62. The heating element 60 thus acts as an evaporator. Vapour/aerosol generated in this way escapes from the microchannels 62 to the outlet side 64 and is mixed with the air flow 34, see FIG. 1. More precisely, upon detection of an air stream 34 caused by the consumer puffing through the air channel 30, the electronic control device 15 controls the heating voltage source 71, wherein the liquid in the microchannels 62 in the form of vapour/aerosol is driven out of the microchannels 62 by spontaneous heating.

The duration of the individual evaporation steps at different temperatures and/or an evaporation of the individual components of the individual portions of the liquid can be kept so short and/or clocked using an activation frequency that the step-by-step evaporation cannot be perceived by a consumer and nevertheless a largely homogeneous, taste-consistent, repeatable precise aerosol formation can be ensured. In particular, it is advantageous to first evaporate a low-boiling component of the liquid in a first evaporation interval at a first temperature A, and then to evaporate a high-boiling component of the liquid in a second evaporation interval at a second temperature B, which exceeds the first temperature A.

A voltage curve Uh(t) adjusted to the liquid mixture used is preferably stored in the data store of the inhaler 10. This makes it possible to set the voltage curve Uh(t) according to the liquid used, so that the heating temperature of the heating element 60, and therefore also the temperature of the capillary microchannels 62, can be controlled in accordance with the known evaporation kinetics of the respective liquid over time during the evaporation procedure, thus achieving optimum evaporation results. The evaporation temperature is preferably in the range between 100° C. and 400° C., more preferably between 150° C. and 350° C., even more preferably between 190° C. and 290° C.

A porous and/or capillary, liquid-conducting wick structure 19 is arranged on the inlet side 61 of the heating element 60. The wick structure 19 contacts the inlet side 61 of the heating element 60 over a surface and covers all microchannels 62 on the inlet side, as can be seen in FIG. 2. On the side opposite the heating element 60, the wick structure 19 is connected to the liquid store 18 in a fluid-conducting manner. The direct connection of the liquid store 18 to the wick structure 19 shown in FIGS. 1 and 2 is only to be understood as an example. In particular, a liquid interface and/or a plurality of liquid conduits can be provided between the liquid store 18 and the wick structure 19. The liquid store 18 can therefore also be arranged at a distance from the wick structure 19. The dimensions of the liquid store 18 can be larger than those of the wick structure 19. The wick structure 19 can, for example, be inserted into an opening in a housing of the liquid store 18. A plurality of evaporator units 20 can also be associated with a liquid store 18.

The wick structure 19 consists of porous and/or capillary material which, due to capillary forces, is able to passively convey sufficient liquid evaporated from the heating element 60 from the liquid store 18 to the heating element 60 in order to prevent the microchannels 62 from running empty and to prevent problems resulting therefrom.

The wick structure 19 consists advantageously of a non-conductive material in order to avoid an undesired heating of the liquid in the wick structure 19 by current flow. If the wick structure 19 consists of a conductive material, which is not excluded, an insulating layer of an electrically and/or thermally insulating material, for example glass, ceramic or plastics material, is advantageously provided between the wick structure 19 and the heating element 60, with passage openings extending through the insulating layer and corresponding to the microchannels 62.

The wick structure 19 consists advantageously of one or a plurality of the following materials: cotton, cellulose, acetate, glass fibre fabric, glass fibre ceramic, sintered ceramic, ceramic paper, aluminosilicate paper, metal foam, metal sponge, another heat-resistant, porous and/or capillary material having a suitable conveying rate, or a combination of two or a plurality of the materials mentioned above. In an advantageous practical embodiment, the wick structure 19 may comprise at least one ceramic fibre paper and/or one porous ceramic. The volume of the wick structure 19 is preferably in the range between 1 $mm^3$ and 10 $mm^3$, more preferably in the range between 2 $mm^3$ and 8 $mm^3$, even more preferably in the range between 3 $mm^3$ and 7 $mm^3$ and is, for example, 5 $mm^3$.

The wick structure 19 can generally consist of one or a plurality of parts.

The heating element 60 can be advantageously manufactured from parts of a wafer using thin film layer technology, which has a layer thickness of preferably less than or equal to 1000 μm, more preferably less than or equal to 750 μm, even more preferably less than or equal to 500 μm. Surfaces of the heating element 60 can advantageously be hydrophilic. The outlet side 64 of the heating body 60 can advantageously be microstructured or have micro grooves.

The evaporator unit 20 is set in such a manner that a quantity of liquid is added preferably in the range between 1 μl and 20 μl, more preferably between 2 μl and 10 μl, even more preferably between 3 μl and 5 μl, typically 4 μl per puff by the consumer. The evaporator unit 20 can preferably be adjustable in terms of the amount of liquid/vapour per puff.

Figure 3:
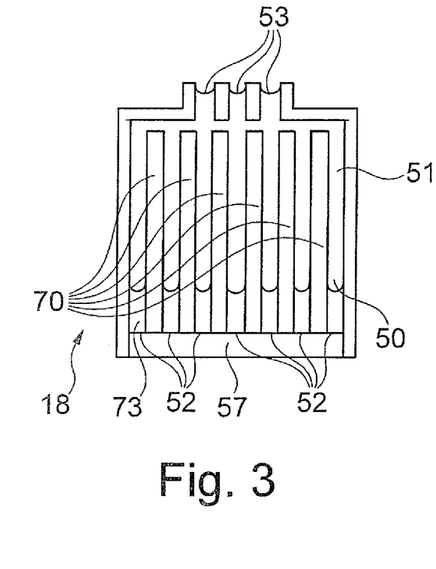
FIGS. 3, 4 are schematic representations of an embodiment of a liquid store.
Figure 4:
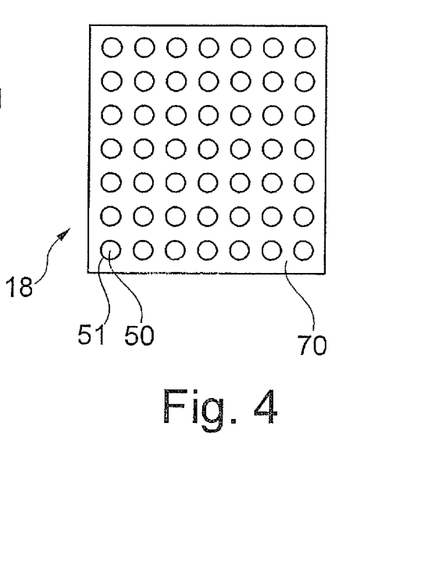

FIGS. 3 and 4 show sections through different levels of a schematic representation of an embodiment of a liquid store 18 which has a rectangular cross section. The liquid store 18 comprises a plurality of outlet ends 53, a plurality of air inlet ends 52 and a plurality of channels 51 extending between the outlet ends 53 and air inlet ends 52. The channels 51 are separated from one another by channel walls 70, 75 and/or extend through or are formed by the channel walls 70, 75. The plurality of air inlet ends 52 are coupled to the outside world through a semipermeable seal and/or filter layer 57. The semipermeable seal and/or filter layer 57 allows air 73 to enter the channel 51 through the air inlet ends 52 and thus into the liquid store 18. The number and geometry of the outlet ends 53 are adapted to the respective wick 19.

In the channels 51, the liquid store 18 contains liquid 50 and possibly air 73 which has penetrated into the liquid store due to the consumption of liquid 50. In a factory-made condition, the liquid store 18 preferably contains only liquid 50 and no air 73.

Figure 5:
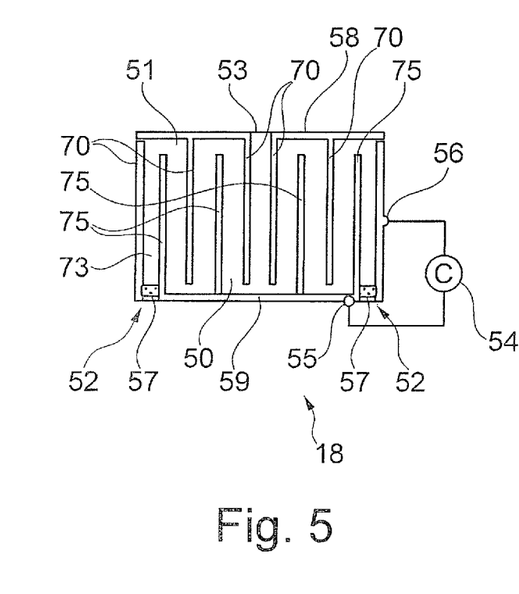
FIGS. 5, 6 are schematic representations of a further embodiment of a liquid store.
Figure 6:
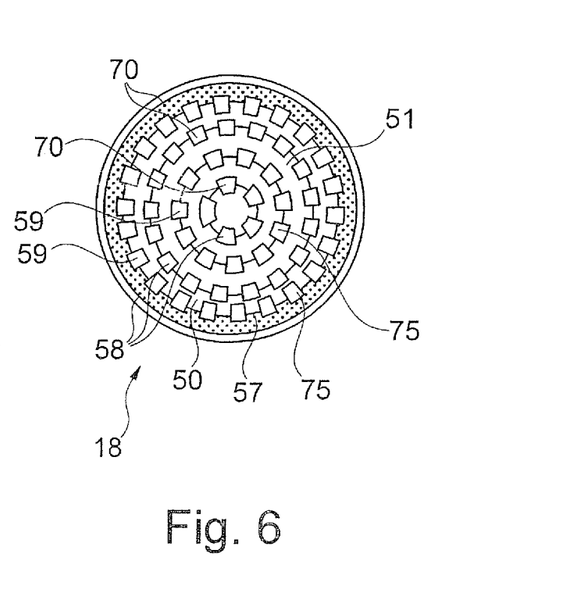

A plurality of channels 51 can be arranged in the form of pores or holes as an array in embodiments that are not shown. The channels 51 can also be cylindrically coaxial, interlocking or interlocking in portions. Correspondingly, the channel walls 70, 75 can have a round, square, rectangular or any other cross section. The at least one channel 51 can advantageously be stretched or "rolled up" in any shape, see FIG. 6, or arranged in a spiral. FIGS. 5 and 6 show sections through different levels of a schematic representation of a further embodiment of a liquid store 18 with a round, preferably circular, cross section. In this embodiment, an outlet end 53 is arranged in the middle of the circular cross section of the liquid store 18. In this embodiment, the liquid store 18 has an air inlet end 52, which is ring-shaped around the circumference of the circular liquid store 18. A channel 51 extends between the outlet end 53 and the air inlet end 52. The geometry of the channel 51 is determined by channel walls 70, 75. The air inlet end 52 is coupled to the outside world by an annular, semipermeable seal and/or filter layer 57. The semipermeable seal and/or filter layer 57 allows air 73 to enter through the air inlet end 52 into the channel 51 and thus into the liquid store 18, but inhibits the exit of liquid 50 from the liquid store 18.

In this embodiment, the liquid store 18 consists of two housing parts 58, 59. The housing parts 58, 59 interlock in a comb-like manner, i.e. as can be seen in FIG. 5, each of the housing parts 58, 59 comprises a base which is arranged at the top or bottom in this view and tines extending perpendicularly to the base and formed by the channel walls 70, 75, in such a way that the tines of the housing parts 58, 59 are arranged opposite to each other and interlock like two combs.

FIG. 6 shows that the comb-like interlocking of the two housing parts 58, 59 has the consequence that the channel walls 70, 75 are alternately formed by one of the housing parts 58, 59. A part of the channel walls 70 is preferably formed by the housing part 58 and/or a part of the channel walls 75 is preferably formed by the housing part 59. The channel 51 is thus formed by cylindrically coaxial housing parts 58, 59 which are intertwined or interlocked in portions. The channel 51 is formed between the housing parts 58, 59 in which the liquid 50 and possibly the air 73 are stored and/or transported.

Furthermore, the embodiment of the liquid store 18 shown in FIGS. 5 and 6 has a fill level sensor 54, preferably a capacitive fill level sensor 54. The fill level sensor 54 is equipped with at least one measuring electrode 55, 56 to carry out fill level measurements of the liquid store 18. In this embodiment, the fill level sensor 54 is connected to the housing part 59 via a measuring electrode 55 and to the housing part 58 via a further measuring electrode 56. The fill level sensor 54 is therefore advantageously connected between the housing parts 58, 59 acting as electrodes. The housing parts 58, 59 are preferably made of an electrically conductive material in order to serve as electrodes for the in particular capacitive and/or resistive measurement of the fill level sensor 54. The liquid 50 located in the channel 51 between the housing parts 58, 59 and the air 73 possibly located in the channel 51 represent a dielectric for the capacitive measurement. The liquid 50 and the air 73 have different dielectric constants and thus bring about a level-dependent electrical capacitance change in the liquid store 18.

The removal of liquid 50 at the heater-side opening, i.e. at the at least one outlet end 53, can take place actively or passively. A "passive withdrawal" means the withdrawal of liquid 50 from the liquid store 18 solely on the basis of thermodynamic and/or hydrodynamic processes, in particular capillary forces and/or Laplace pressure. An "active withdrawal" means the withdrawal of liquid 50 from the liquid store 18, which is supported by active, in particular electromechanical, components.

The removal can be actively controlled by the evaporator unit 20, and/or other elements such as valves and pumps can be set up for an active removal of liquid 50 from the liquid store 18. The active and/or passive removal of liquid 50 builds up a negative Laplace pressure. The negative Laplace pressure can be built up on the outlet side, i.e. close to the outlet end 53, by means of a hydrophilic wall portion of a channel wall 70, 75 or a capillary wick 19 or any porous material.

The end facing away from the heating element 60, i.e. the at least one air inlet end 52, is provided with the semipermeable seal 57, which preferably allows air 73 to penetrate into the liquid store 18, but does not allow any liquid 50 to escape from the liquid store 18. The semipermeable seal 57 can be, for example, a hydrophobic sponge or a porous ceramic.

Figure 7:
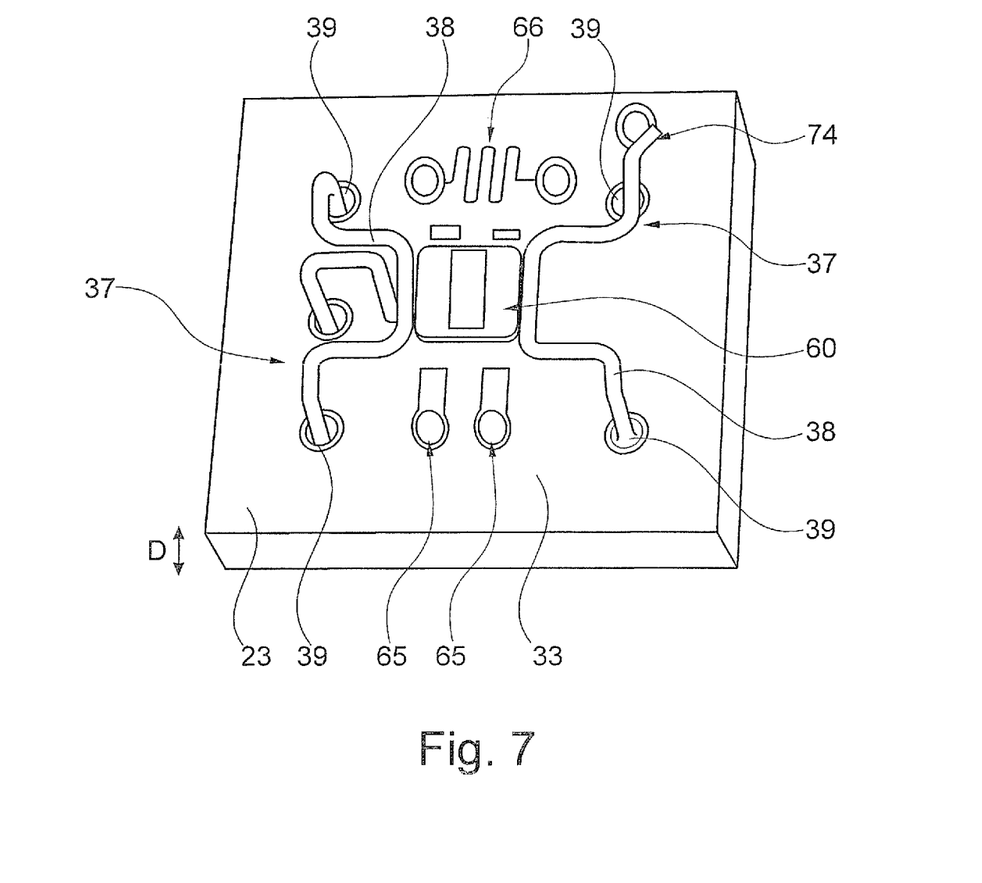
FIG. 7 is a heating element on a carrier having a sensor for the detection of liquid and a temperature sensor.

As shown in FIG. 7, the evaporator unit 20 advantageously has a carrier 23, in particular in the form of a plate, for supporting the heating element 60. The carrier 23 can consist of a suitable material, for example ceramic, glass and/or plastics material, including fibre-reinforced plastics, for example printed circuit board material, and has a passage opening under the heating element 60, which cannot be seen in FIG. 7, through which the wick structure 19 extends downwards in the direction of the liquid store 18.

The dimensions of the carrier 23, which is rectangular for example, are preferably in the range between 6 mm and 20 mm, more preferably in the range between 8 mm and 17 mm and even more preferably in the range between 10 mm and 14 mm. The thickness D of the carrier 23 is preferably in the range between 0.5 mm to 4 mm, more preferably in the range between 1 mm to 3 mm, even more preferably in the range between 1 mm and 2 mm and can be, for example, 1.6 mm or 2 mm.

The heating element 60 is clamped on the carrier 23 by means of at least two clamping elements 37 which engage the heating element 60 on opposite sides thereof. Each clamping element 37 advantageously has a clamping bracket 38 which is resiliently fastened to the carrier 23 at two spaced-apart fastening points 39 and generates a pretension by means of which the heating element 60 is clamped on the carrier 23 and thus held securely.

The clamping elements 37 serve particularly advantageously at the same time as electrodes for contacting the heating element 60 and supplying it with heating current. For this purpose, the clamping elements 37 or the clamping brackets 38 advantageously consist of an electrically conductive material, for example this may be metal wire, for example brass wire. Due to the line contact between the clamping bracket 38 and the heating element 60, there is an excellent electrical connection between the clamping element 37 and the heating element 60, with at the same time ideal thermal decoupling between the clamping element 37 and the heating element 60 due to the lack of surface contact. Heat dissipation from the heating element 60 into the clamping element 37 is therefore low, the electrodes 38 remain significantly cooler than the heating element 60.

The clamping elements 37 can be contacted downwards via bores in the carrier 23 and connected to a printed circuit board (PCB) provided in the consumption unit 17 in order to establish the electrical connection to the electronic control device 15 and to the energy source 14 for the power supply of the heating element 60. In another embodiment, the carrier 23 can form the printed circuit board. It is also possible that the evaporator unit 20 itself does not comprise a printed circuit board, but rather the clamping brackets 38 are connected to a printed circuit board arranged in the base part 16, for example via flexible insulated lines, or in another suitable manner.

FIG. 7 shows a liquid sensor 65 for the detection of liquid and a temperature sensor 66 likewise arranged on the carrier 23. The liquid sensor 65 and the temperature sensor 66 are arranged abutting or on top of the carrier 23. The liquid sensor 65 and/or the temperature sensor 66 is or are advantageously arranged on the same side 33 of the carrier as the outlet side 64 of the heating element.

In this embodiment, the liquid sensor 65 is a capacitive liquid sensor with coplanar electrodes, i.e. the electrodes are arranged in one plane on the upper side 33 of the carrier 23. The temperature sensor 66, in particular a resistive temperature sensor, has a meandering shape here and is designed as a conductor track which is, for example, vapour-deposited directly on the carrier 23. The electrodes of the liquid sensor 65 are also advantageously applied as conductor tracks on the upper side 33 of the carrier 23, which is particularly advantageously a printed circuit board (PCB).

Furthermore, a safety device in the form of an overheating protection 74 can be provided to protect the heating element 60, the liquid 50 and/or sensitive electronic components. The overheating protection 74 can comprise a bimetal strip, for example. The overheating protection 74 can be part of a safety system which comprises sensors and actuators and which detects the presence of liquid 50 on the heating element 60 and measures the temperature in the evaporator unit 20 and controls corresponding safety processes which include, for example, feedback loops including the heating voltage source 71.

The liquid sensor 65 and temperature sensor 66 described provide a safety function which monitors the direct surroundings of the heating element 60. In the event of overheating of the liquid 50 and/or of the heating element 60, for example due to misuse or malfunction, the system can be switched off or countermeasures for cooling can be initiated.

If the liquid sensor 65 reports an insufficient amount of liquid 50 at the heater 60, which can lead to an undesirable increase in the temperature of the heating element 60, the system can, for example, switch to a safety mode and heat with reduced power or switch off the heating element 60.

Exact temperature monitoring in the immediate vicinity of the heating element 60 can be integrated as an additional safety function if, for example, the heating element 60 is set up as a temperature measuring element, as can be the case with a silicon heating element 60, for example.

Furthermore, the aerosol quality can be influenced by the amount of liquid 50 which is supplied to the heating element 60 during an evaporation process, i.e. by the liquid mass flow. The aerosol quality has an influence on the recondensation behaviour of the aerosol. Knowledge of the liquid mass flow and the underlying relationships thus allows a prediction of the probable droplet sizes, taking into account the parameters set on the evaporator unit 20, or the adaptation of these parameters in order to influence the droplet sizes. The liquid mass flow can advantageously be determined by means of the capacitive and/or resistive sensor 65.

The activation frequency of the heating element 60 produced by the heating voltage source 71 is advantageously in the range from 1 Hz to 50 kHz, preferably in the range from 30 Hz to 30 kHz, and even more advantageously in the range from 100 Hz to 25 kHz.

The course of the evaporation procedure is explained below.

The heating voltage source 71 for the heating procedure is switched off in an outlet state.

In order to evaporate liquid 50, the heating voltage source 71 for the heating element 60 is activated. The voltage Uh is set in such a manner that the evaporation temperature in the heating element 60 and therefore in the microchannels 62 is adapted to the individual evaporation behaviour of the liquid mixture used. This prevents the danger of local overheating and thereby the formation of harmful substances.

As soon as a quantity of liquid equal to or related to the volume of the microchannels 62 has evaporated, the heating voltage source 71 is deactivated. Since the liquid properties and amount are advantageously known exactly, this point in time can be controlled very precisely. The energy consumption of the evaporator unit 20 can therefore be reduced compared to known devices, since the required evaporation energy can be dosed and thereby introduced more precisely.

After completion of the heating procedure, the microchannels 62 are predominantly or completely emptied. The heating voltage source 71 is then kept switched off until the microchannels 62 are replenished by feeding liquid 50 from the liquid store 18 through the wick structure 19.

By means of the outlet ends 53, liquid 50 is conveyed from the liquid store 18 to the heating element 60, preferably via the wick 19. As a result of the removal of liquid 50 from the liquid store 18, the liquid store 18 is emptied and a volume of air 73 corresponding to the volume of the removed liquid 50 is sucked into the channel 51 via the at least one air inlet end 52 through the semipermeable seal and/or filter layer 57.

As soon as the microchannels 62 are filled again, the next heating cycle can be started by switching on the heating voltage source 71.

The evaporator unit 20 is preferably produced on the basis of MEMS technology, in particular made of silicon, and is therefore advantageously a micro-electromechanical system.

Embodiments

Embodiment 1. Liquid store for an inhaler (10), in particular for an electronic cigarette product, having an outlet end (53) which can be fluidically connected to a heating element (60) in order to evaporate liquid (50) supplied to the heating element (60) from the liquid store (18), characterised in that the liquid store (18) has at least one air inlet end (52) and at least one channel (51), and the channel (51) extends from the air inlet end (52) to the outlet end (53) through the liquid store (18), wherein the channel (51) is designed to transfer the liquid (50) stored in the liquid store (18) to the outlet end (53) through the channel (51) by means of capillary forces.

Embodiment 2. Liquid store according to any of the preceding embodiments, characterised in that the liquid store (18) has an in particular capacitive and/or resistive fill level sensor (54) which has at least one measuring electrode (55, 56) arranged along the at least one channel (51).

Embodiment 3. Liquid store according to embodiment 2, characterised in that the measuring electrode (55, 56) is formed by an electrically conductive part of the liquid store (18).

Embodiment 4. Liquid store according to any of the preceding embodiments, characterised in that a semipermeable seal and/or filter layer (57) is arranged on the at least one air inlet end (52), wherein the semipermeable seal and/or filter layer (57) is air-permeable and liquid-impermeable.

Embodiment 5. Liquid store according to any of the preceding embodiments, characterised in that the liquid store (18) has a plurality of channels (51).

Embodiment 6. Liquid store according to any of the preceding embodiments, characterised in that the at least one channel (51) is formed between at least two housing parts (58, 59) of the liquid store (18), each having at least one channel wall (70, 75), the channel walls (70, 75) interlocking in a comb-like manner when the housing parts (58, 59) are assembled.

Embodiment 7. Liquid store according to embodiment 6, characterised in that the housing parts (58, 59) consist of an electrically conductive material or are coated with an electrically conductive material.

Embodiment 8. Liquid store according to any of the preceding embodiments, characterised in that the at least one channel (51) has regions of different hydrophilicity and/or hydrophobicity.

Embodiment 9. Liquid store according to claim 8, characterised in that the at least one channel (51) at the air inlet end (52) has a lower hydrophilicity than at the outlet end (53).

Embodiment 10. Liquid store according to either embodiment 8 or embodiment 9, characterised in that the at least one channel (51) at the air inlet end (52) is hydrophobic.

Embodiment 11. Liquid store according to any of embodiments 8 to 10, characterised in that the at least one channel (51) at the outlet end (53) is hydrophilic.

Embodiment 12. Consumption unit (17) for an inhaler (10), comprising a liquid store (18) according to any of the preceding claims, and an evaporator unit (20) having the electrically operable heating element (60), the heating element (60) being arranged to evaporate liquid (50) conveyed from the liquid store (18) to the heating element (60) by applying a heating voltage.

Embodiment 13. Consumption unit according to embodiment 12, characterised in that a wick structure (19) is arranged between the heating element (60) and the liquid store (18), the wick structure (19) being set up absorb liquid (50) from the at least one outlet end (53) of the liquid store (18) and to convey it to the heating element (60) by means of capillary forces.

Embodiment 14. Consumption unit according to embodiment 13, characterised in that the wick structure (19) covers the outlet end or all of the outlet ends (53).

Embodiment 15. Consumption unit according to any of the preceding embodiments, characterised in that at least one in particular capacitive and/or resistive sensor (65) for detecting liquid is arranged on the heating element (60).

Embodiment 16. Consumption unit according to any of the preceding embodiments, characterised in that at least one in particular resistive temperature sensor (66) for measuring the temperature of the heating element (60) and/or the air (34) flowing past the heating element (60) is set up on the heating element (60).

Embodiment 17. Consumption unit according to embodiment 16, characterised in that the temperature sensor (66) has a meandering shape.

Embodiment 18. Consumption unit according to embodiment 16, characterised in that the temperature sensor (66) is formed by the heating element (60).

Embodiment 19. Consumption unit according to any of embodiments 15 to 18, characterised in that at least one of the sensors (65, 66) is designed as a conductor track on a carrier (23) for the heating element (60).

Embodiment 20. Consumption unit according to embodiment 19, characterised in that at least one of the sensors (65, 66) is arranged on the same side (33) of the carrier (23) as the heating element (60).

The invention claimed is:

1. A liquid store for an inhaler, comprising:
   an outlet end, wherein the outlet end is configured to be fluidically connected to a heating element in order to evaporate liquid supplied to the heating element from the liquid store;
   at least one air inlet end;
   one or more channel walls; and
   at least one channel, wherein the at least one channel extends from the at least one air inlet end to the outlet end, wherein the channels of the at least one channel are separated from one another by, extend through, or are formed by the one or more channel walls, and wherein the at least one channel is configured to transfer liquid stored in the liquid store to the outlet end through the at least one channel via capillary forces.

2. The liquid store according to claim 1, further comprising:
   a capacitive and/or resistive fill level sensor which has at least one measuring electrode arranged along the at least one channel.

3. The liquid store according to claim 2, wherein the at least one measuring electrode is formed by an electrically conductive part of the liquid store.

4. The liquid store according to claim 3, wherein a semipermeable seal and/or filter layer is arranged on the at least one air inlet end, and wherein the semipermeable seal and/or filter layer is air-permeable and liquid-impermeable.

5. The liquid store according to claim 1,
   wherein the at least one channel comprises a plurality of channels.

6. The liquid store according to claim 1, further comprising:
   at least two housing parts, each having at least one channel wall of the one or more channel walls, with the at least one channel wall of the at least two housing parts interlocking in a comb-like manner when the at least two housing parts are assembled,
   wherein the at least one channel is formed between the at least two housing parts.

7. The liquid store according to claim 6, wherein the at least two housing parts consist of an electrically conductive material or are coated with an electrically conductive material.

8. The liquid store according to claim 1, wherein the at least one channel has regions of different hydrophilicity and/or hydrophobicity.

9. The liquid store according to claim 8, wherein the at least one channel has a lower hydrophilicity at the at least one air inlet end than at the outlet end.

10. The liquid store according to claim 8, wherein the at least one channel is hydrophobic at the at least one air inlet end.

11. The liquid store according to claim 1, wherein the at least one channel is hydrophilic at the outlet end.

12. A consumption unit for an inhaler, comprising:
the liquid store according to claim 1; and
an evaporator unit having an electrically operative heating element, the electrically operative heating element being arranged to evaporate liquid conveyed from the liquid store to the electrically operative heating element by applying a heating voltage.

13. The consumption unit according to claim 12, wherein a wick structure is arranged between the electrically operative heating element and the liquid store, the wick structure being set up to absorb liquid from the outlet end of the liquid store and to convey the liquid to the electrically operative heating element via capillary forces.

14. The consumption unit according to claim 13, wherein the wick structure covers the outlet end.

15. The consumption unit according to claim 12, wherein at least one capacitive and/or resistive sensor for detecting liquid is arranged on the electrically operative heating element.

16. The consumption unit according to claim 12, wherein at least one resistive temperature sensor that measures the temperature of the electrically operative heating element and/or the air flowing past the electrically operative heating element is set up on the electrically operative heating element.

17. The consumption unit according to claim 16, wherein the at least one resistive temperature sensor has a meandering shape.

18. The consumption unit according to claim 16, wherein the at least one resistive temperature sensor is formed by the electrically operative heating element.

19. The consumption unit according to claim 16, wherein one or more resistive temperature sensors of the at least one resistive temperature sensor is designed as a conductor track on a carrier for the electrically operative heating element.

20. The consumption unit according to claim 19, wherein one or more resistive temper sensors of the at least one resistive temperature sensor is arranged on the same side of the carrier as the electrically operative heating element.

* * * * *